US009423438B2

(12) United States Patent
Lin et al.

(10) Patent No.: US 9,423,438 B2
(45) Date of Patent: Aug. 23, 2016

(54) DIELECTRIC CONSTANT MEASUREMENT CIRCUIT AND DIELECTRIC CONSTANT MEASUREMENT METHOD

(71) Applicants: NATIONAL TAIWAN UNIVERSITY, Taipei (TW); National Taiwan University of Science and Technology, Taipei (TW)

(72) Inventors: Chii-Wann Lin, Taipei (TW); Sheng-Yu Peng, Taipei (TW); Bo-Shen Chen, Taipei (TW); Jhih-Hong Lin, Taipei (TW)

(73) Assignees: NATIONAL TAIWAN UNIVERSITY, Taipei (TW); NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 396 days.

(21) Appl. No.: 14/100,027

(22) Filed: Dec. 9, 2013

(65) Prior Publication Data

US 2015/0042358 A1    Feb. 12, 2015

(30) Foreign Application Priority Data

Aug. 12, 2013   (TW) .............................. 102128863 A

(51) Int. Cl.
G01R 27/02    (2006.01)
G01R 27/26    (2006.01)
G01N 33/02    (2006.01)

(52) U.S. Cl.
CPC ............ *G01R 27/2623* (2013.01); *G01N 33/02* (2013.01)

(58) Field of Classification Search
CPC ........................... G01R 27/2623; G01N 33/02
USPC ........................................................ 324/629
See application file for complete search history.

(56) References Cited

U.S. PATENT DOCUMENTS

2012/0150000 A1    6/2012   Al-Shamma'a et al.

FOREIGN PATENT DOCUMENTS

TW             I320150 B      2/2010

OTHER PUBLICATIONS

V. Sekar et al., "A Self-Sustained Microwave System for Dielectric-Constant Measurement of Lossy Organic Liquids," in IEEE Transactions on Microwave Theory and Techniques, vol. 60, No. 5, pp. 1444-1455, May 2012.
A. Helmy et al., "A 1-8-GHz Miniaturized Spectroscopy System for Permittivity Detection and Mixture Characterization of Organic Chemicals," in IEEE Transactions on Microwave Theory and Techniques, vol. 60, No. 12, pp. 4157-4170, Dec. 2012.
A. A. Helmy et al., "A Self-Sustained CMOS Microwave Chemical Sensor Using a Frequency Synthesizer," in IEEE Journal of Solid-State Circuits, vol. 47, No. 10, pp. 2467-2483, Oct. 2012.
F.-C. Chang et al., "A Novel design of Antenna for biosensing applications," 14th International Meeting on Chemical Sensors(IMCS 2012), May 20-23, 2012.

*Primary Examiner* — Melissa Koval
*Assistant Examiner* — Courtney McDonnough
(74) *Attorney, Agent, or Firm* — CKC & Partners Co., Ltd.

(57) ABSTRACT

A dielectric constant measurement circuit includes a dielectric constant sensor, an oscillator controlling circuit, a waveform converting circuit, and a counting readout circuit. The oscillator controlling circuit generates an oscillation waveform according to the response of the dielectric constant sensor to a dielectric material. The waveform converting circuit converts the oscillation waveform into frequency division square waves. The counting readout circuit includes a switching counter, a switching circuit, a reference current source, and a current integrator. The reference current source charges the current integrator through the switching circuit controlled by the frequency division square waves, and the switching counter counts the number of the turned-on states of the switching circuit and stops counting the number of the turned-on states when a value of the output voltage from the current integrator reaches a value of the reference voltage, and the number of the turned-on states is related to the oscillation frequency.

10 Claims, 6 Drawing Sheets

DIELECTRIC CONSTANT MEASUREMENT CIRCUIT AND DIELECTRIC CONSTANT MEASUREMENT METHOD

RELATED APPLICATIONS

This application claims priority to Taiwan Application Serial Number 102128863, filed Aug. 12, 2013, which is herein incorporated by reference.

BACKGROUND

1. Field of Invention

The present invention relates to a measurement circuit. More particularly, the present invention relates to a dielectric constant measurement circuit and a dielectric constant measurement method.

2. Description of Related Art

The general dielectric constant measurement system needs using the expensive and heavy network analyzer to measure the offset frequency and the return loss parameter of the oscillator, but the network analyzer cannot be integrated into the general consumer electronics.

In general, integrated circuits are utilized to construct a phase locked loop (PLL) serving as the interface circuit of the sensing system. The interface circuit reads the value of the controlling voltage from the voltage-controlling oscillator, and then the analog-digital converter converts the frequency information into the digital signal. The analog-digital converter will restrict the readout frequency resolution of this system, and it will need an exactly standard reference frequency signal.

The conventional dielectric constant measurement system must be applied with the large instrument to read the oscillation frequency and the quality factor of the oscillator. But analog-to-digital converter embedded in the dielectric constant measurement system will restrict the resolution and consume more power. Therefore, it is one of the important subjects and the objective needs to increase the resolution of readout frequency, to reduce the power consumption and further to integrate the dielectric constant measurement system into the integrated circuit.

SUMMARY

A dielectric constant measurement circuit and a dielectric constant measurement method are provided to resolve the problems of the prior art.

The dielectric constant measurement circuit comprises a dielectric constant sensor, an oscillator controlling circuit, a waveform converting circuit, and a counting readout circuit. The oscillator controlling circuit is electrically connected to the dielectric constant sensor and comprises an oscillator. The oscillator controlling circuit is configured to generate an oscillation waveform according to a variation of a real number part and an imaginary number part in a dielectric constant of a dielectric material when a dielectric constant sensor senses a dielectric material. The waveform converting circuit is electrically connected to the oscillator controlling circuit and is configured to convert the oscillation waveform into a plurality of frequency division square waves. The counting readout circuit is electrically connected to the waveform converting circuit and comprises a switching counter, a switching circuit, a reference current source, and a current integrator. The turn-on/off states of the switching circuit are controlled by the frequency division square waves so that the reference current source charges the current integrator intermittently through the switching circuit. The switching counter counts the number of the turned-on states of the switching circuit. The switching counter stops counting the number of the switching circuit opening when a value of the output voltage from the current integrator reaches a value of the reference voltage, and the number of the turned-on states of the switching circuit reflects the oscillation frequency.

A dielectric constant measurement method comprises: generating an oscillation waveform according to a variation of a real number part and an imaginary number part in a dielectric constant of a dielectric material when a dielectric constant sensor senses a dielectric material; converting the oscillation waveform into a plurality of frequency division square waves; controlling the turn-on/off states of a switching circuit based on the frequency division square waves so that the reference current source charges the current integrator intermittently through the switching circuit, counting the number of the turned-on states of the switching circuit, stopping counting the number of the turned-on states of the switching circuit when an output voltage of the current integrator reaching a value of the reference voltage, and the number of the turned-on states of the switching circuit related to the oscillation frequency.

In summary, the technical solutions of the present invention have obvious advantages and beneficial effects over the prior art. With the above technical solutions, considerable advances of technology and extensive utilization in industry can be achieved. The present invention has an advantage in that using the counter in order to increase the resolution of readout frequency if increasing the readout time so that no need the extra designed analog-digital converter that restricts the resolution of readout frequency. Furthermore, the present invention is able to reduce the power consumption of the special analog-digital converter, save the cost of the chip area, lessen the impact likelihood risk of the phase noise of the oscillator, have the elastic usage, integrate to the integrated circuit, and make miniaturization. The conventional expensive and heavy dielectric constant measurement instrument is not needed, and the present invention is even able to integrate in consumption communication products in order to apply in life.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
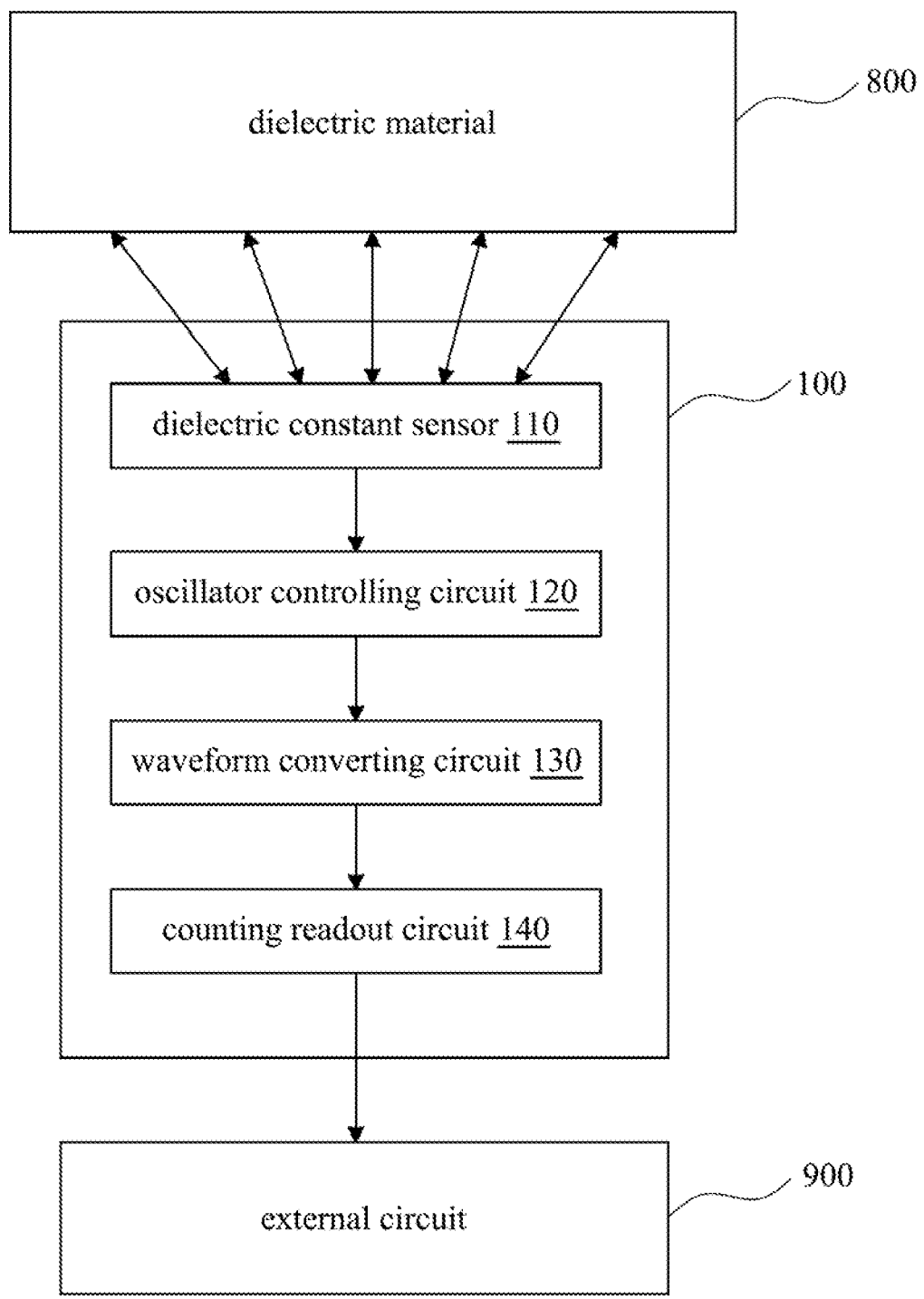
FIG. 1 is a schematic diagram of a dielectric constant measurement circuit according to an embodiment of the present invention.

Reference will now be made in detail to the present embodiments of the invention, examples of which are illustrated in the accompanying drawings. Wherever possible, the same reference numbers are used in the drawings and the description to refer to the same or like parts. In addition, the well-known components and steps are not described in the embodiments to avoid unnecessary limitations to the present invention.

FIG. 1 is a schematic diagram of a dielectric constant measurement circuit 100 according to an embodiment of the present invention. As shown in FIG. 1, the dielectric constant measurement circuit 100 comprises a dielectric constant sensor 110, an oscillator controlling circuit 120, a waveform converting circuit 130, and a counting readout circuit 140. The dielectric constant measurement circuit 100 may measure the dielectric constant of a dielectric material 800 through the non-invasive method to get the component formulation and content of the dielectric material 800; for example, the component and freshness of the food or the drink is measured for detecting the water content of the skin for the biomedical science application, etc.

In structure, the oscillator controlling circuit 120 is electrically connected to the dielectric constant sensor 110, the waveform converting circuit 130 is electrically connected to the oscillator controlling circuit 120, and the counting readout circuit 140 is electrically connected to the waveform converting circuit 130. In practice, the dielectric constant sensor 110 contacts the under test dielectric material 800 by the non-invasive way, so the dielectric constant sensor 110 and the under test dielectric material 800 form a loop. The dielectric constant sensor 110 sends out the wireless sensing signal (such as electromagnetic wave) or wire sensing signal (such as other voltage or current signal) to the under test dielectric material 800. The under test dielectric material 800 may generate the response due to the composition of the under test dielectric material 800. The dielectric constant sensor 110 receives the response and transmits it to the oscillator controlling circuit 120 for processes. The oscillator controlling circuit 120 includes an oscillator 123. The dielectric constant of the dielectric material 800 is a complex number which includes a real number part and an imaginary number part. The oscillator 123 generates an oscillation waveform according to a variation of the real number part and the imaginary number part included in the dielectric constant when the dielectric constant sensor 110 senses the dielectric material 800. The real number part is a dielectric coefficient that may affect the frequency of the oscillation waveform. The imaginary number part is a quality factor that may affect the amplitude of the oscillation waveform. The frequency and the amplitude of the oscillation waveform can be analyzed and processed to identify the type of the dielectric material 800. The oscillation waveform generated from the oscillator controlling circuit 120 may be transmitted to the waveform converting circuit 130, and the waveform converting circuit 130 may convert and divide the oscillation waveform into a plurality of frequency division square waves.

Figure 5:
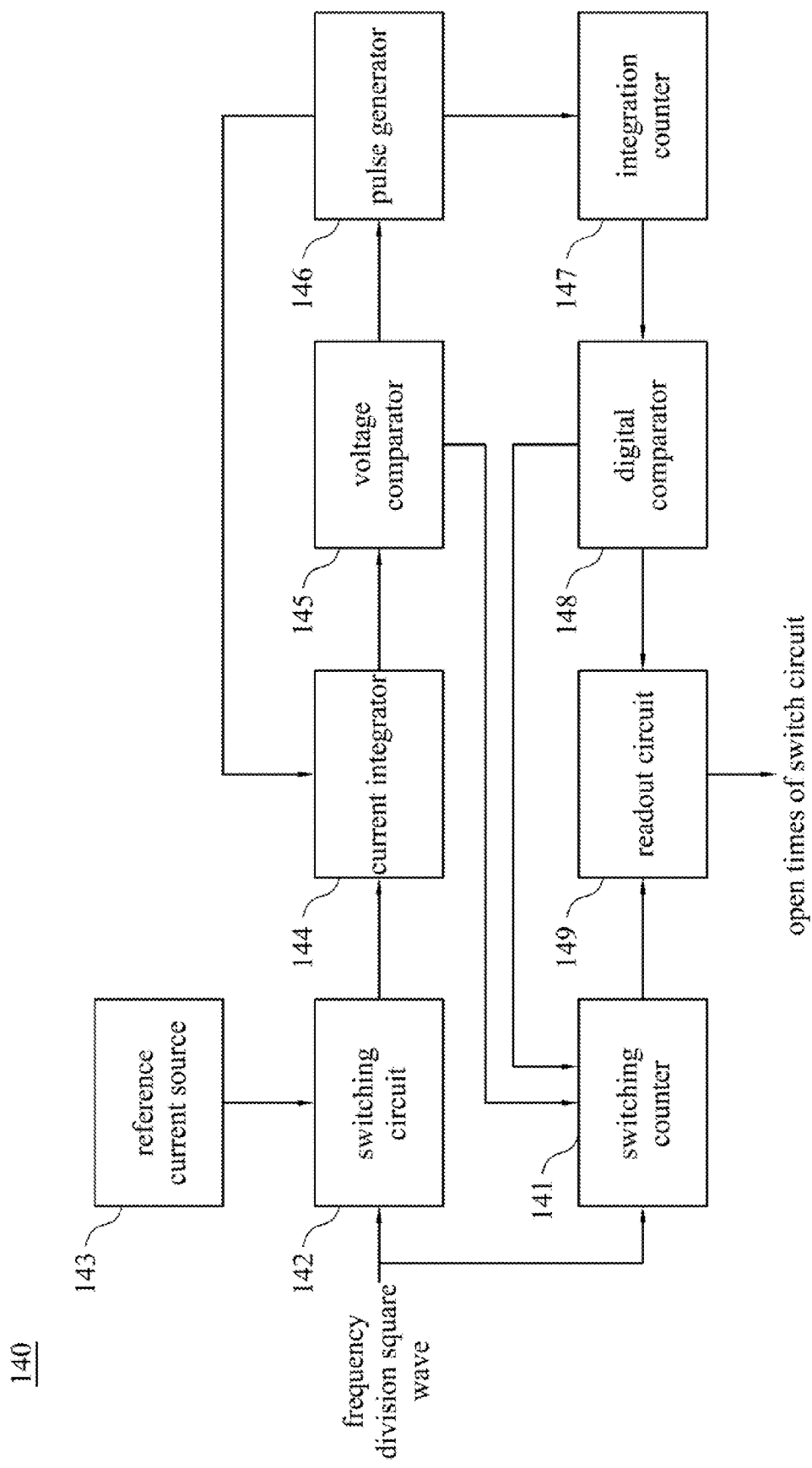
FIG. 5 is a schematic diagram showing a counting readout circuit in FIG. 1 according to an embodiment of the present invention.

The plurality of frequency division square waves generated from the waveform converting circuit 130 may be transmitted to the counting readout circuit 140. FIG. 5 is a schematic diagram showing a counting readout circuit in FIG. 1 according to an embodiment of the present invention. As shown in FIG. 5, in structure, the counting readout circuit 140 comprises a switching counter 141, a switching circuit 142, a reference current source 143, and a current integrator 144. In practice, the turned-on/off states of the switching circuit 142 are controlled by the frequency division square waves. The switching circuit 142 can be turned on when the frequency division square waves change from low level to high level and can be turned off when the frequency division square waves change from high level to low level. The switching circuit 142 is associated with the reference current source 143. When the switching circuit 142 is turned on, the reference current source 143 charges the current integrator intermittently through the switching circuit 142. On the other hand, the switching counter 141 counts the number of the turned-on states of the switching circuit 142.

The current integrator 144 comprises a charging input terminal and a standard input terminal. An initial value of an output voltage from the current integrator 144 is equal to the fixed voltage value of the standard input terminal of the current integrator 144. The current of the reference current source 143 may flow to the charging input terminal of the current integrator 144 and charge the current integrator 144 when the switching circuit 142 is turned on. The value of the output voltage from the current integrator 144 may be changed, i.e., the value of the output voltage is changed once the switching circuit 142 is turned on. When the switching circuit 142 is turned off, the current of the reference current source 143 may not flow to the charging input terminal of the current integrator 144, and the value of the output voltage from the current integrator 144 may stop changing temporarily. The frequency of the frequency division square waves is lower, the turned-on/off time of the switching circuit 142 is longer each period, and the changing time and the suspended changing time of the current integrator 144 is also longer, i.e., the variation of the value of the output voltage from the current integrator 144 is more each period. Accordingly, the changing speed of the value of the output voltage from the current integrator 144 is inversely proportional to the frequency of the frequency division square waves.

The value of the output voltage from the current integrator 144 keeps changing due to the reference current source 143 that is controlled by the switching circuit 142. The switching counter 141 stops counting the number of the turned-on states of the switching circuit 142 when the value of the output voltage from the current integrator 144 reaches a default setting value of a reference voltage. The number of the turned-on states may calculate an oscillation frequency of the oscillation waveforms through an external circuit 900. For example, the dielectric constant measurement circuit 100 may be an integrated circuit installed in a portable device (such as, a mobile, a tablet computer), and the external circuit 900 may be the system circuit in the portable device. The external circuit 900 can calculate the oscillation frequency of the oscillation waveforms based on the number of the turned-on states of the switching circuit 142, the time from the initial value of the output voltage to the value of the reference voltage for the output voltage from the current integrator 144, and the other relative adjustable parameters.

Figure 2:
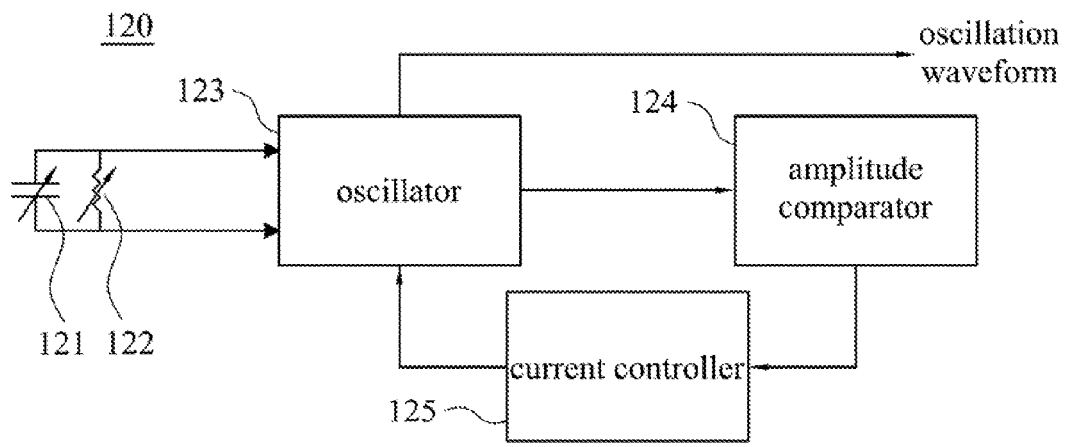
FIG. 2 is a schematic diagram showing an oscillator controlling circuit in FIG. 1 according to an embodiment of the present invention.

The dielectric constant sensor 110 converts the response based on the dielectric material 800 into more parameters that may be processed by the dielectric constant measurement circuit 100 and analyzes these parameters to achieve the purpose of distinguishing the dielectric material 800. In an embodiment, the dielectric constant sensor 110 generates the waveform based on the response of the dielectric material 800 and analyzes the waveform in order to achieve the purpose of distinguishing the dielectric material 800. FIG. 2 is a schematic diagram showing an oscillator controlling circuit 120 in FIG. 1 according to an embodiment of the present invention. As shown in FIG. 2, the oscillator controlling circuit 120 comprises an oscillator 123, an amplitude comparator 124, and a current controller 125. In structure, the oscillator 123 is electrically connected to the dielectric constant sensor 110, the amplitude comparator 124 is electrically connected to the oscillator 123, and the current controller 125 is electrically connected to the oscillator 123 and the amplitude comparator 124. In practice, the different dielectric materials 800 has the different dielectric constants based on the internal constituents each dielectric material 800. The oscillator 123 generates the oscillation waveform according to the variation of the real number part and the imaginary number part in the dielectric constant of the dielectric material when the dielectric constant sensor 110 senses the dielectric material 800. The real number part may affect the value of the equivalent variable capacitor 121 in the oscillator 123, and the imaginary number part may affect the value of the equivalent variable resistance 122 in the oscillator 123. The value of the equivalent variable resistance 122 is related to the quality factor of the oscillation waveform to calculate the quality factor of the dielectric constant of the dielectric material 800. The value of the equivalent variable capacitor 121 is related to the frequency of the oscillation waveform to calculate the dielectric coefficient of the dielectric constant of the dielectric material 800.

In an embodiment, in order to control the oscillation waveform within the range that can be processed and analyzed by the dielectric constant measurement circuit 100 of the present invention, the amplitude value of the oscillation waveform may be controlled at the fixed amplitude value. The amplitude comparator 124 compares the amplitude value of the oscillation waveform with the reference value that has been set in the amplitude comparator 124 and generates a compared result. The current controller 125 sends a controlling signal according to the compared result to adjust a bias current and controls the amplitude value of the oscillation waveform at the fixed value, and the method is a negative feedback control. So, the current controller 125 corrects the amplitude value of the oscillation waveform through the negative feedback controlling. The power consumption of the oscillation 123 oscillating may affect the value of the equivalent variable resistance 122 in the oscillator 123. The power consumption is more, and the value of the equivalent variable resistance 122 is smaller. The amplitude of the oscillation 123 will be smaller when the power consumption of the oscillation 123 is more because the dielectric constant sensor 110 receives the response of the dielectric material 800. The current controller 125 will generate more current to stabilize the oscillation waveform of the oscillator 123, i.e., adjusting the amplitude of the oscillation waveform at the fixed value. It is therefore clear that the controlling signal of the current controller 125 may be related to the value of the equivalent variable resistance 122 in the oscillation 123 due to the response of the dielectric material 800. The value of the equivalent variable resistance 122 is related to the quality factor of the oscillation waveform, so it can be used to calculate the quality factor of the dielectric constant of the dielectric material 800.

Figure 3:
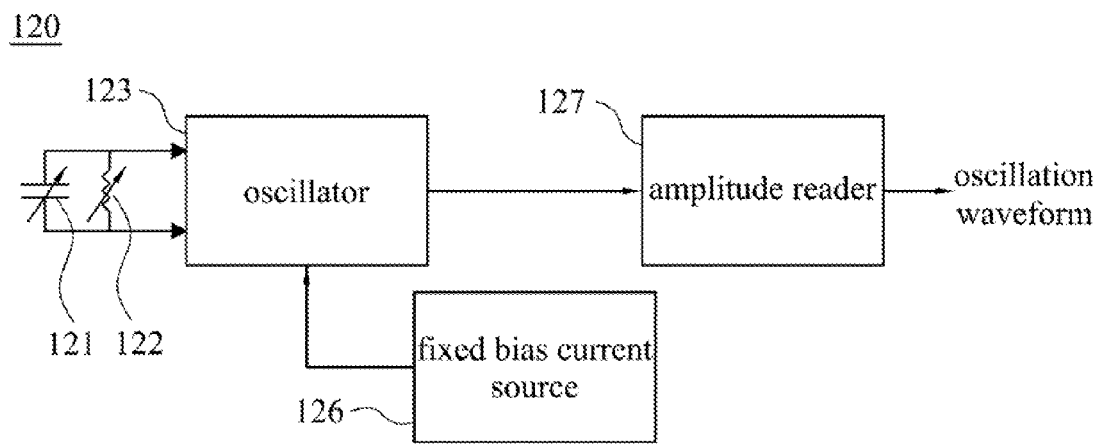
FIG. 3 is a schematic diagram showing an oscillator controlling circuit in FIG. 1 according to another embodiment of the present invention.

As shown in FIG. 3, in an alternative embodiment, a fixed bias current source 126 is electrically connected to the oscillation 123 and provides a fixed bias current to oscillation 123. An amplitude reader 127 is electrically connected to the oscillation 123 and reads the amplitude of the oscillation waveform. This embodiment is also able to calculate the quality factor of the dielectric constant of the dielectric material 800.

Figure 4:
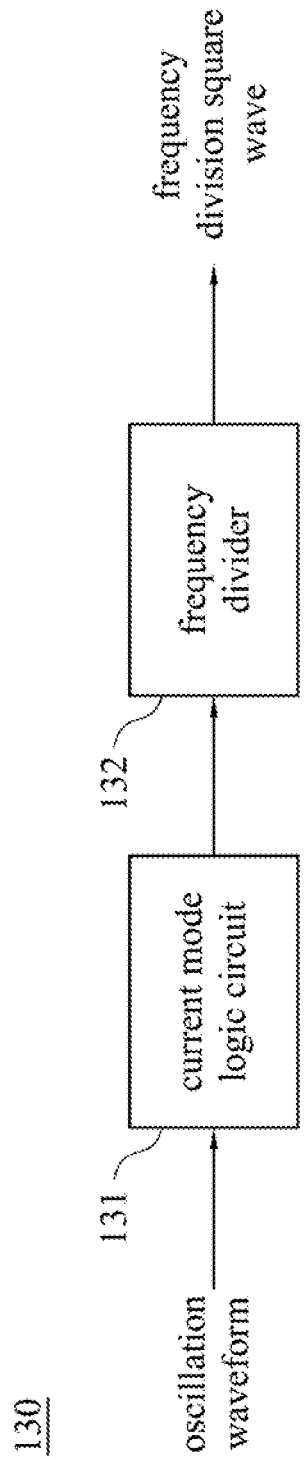
FIG. 4 is a schematic diagram showing a waveform converting circuit in FIG. 1 according to an embodiment of the present invention.

In order to control the switching circuit 142 of the counting readout circuit 140 correctly, the oscillation waveform is converted into the oscillation square wave that can control the switching circuit 142 easier then converted into the frequency division square waves that are able to make the action of the switching circuit 142 correctly. FIG. 4 is a schematic diagram showing a waveform converting circuit 130 in FIG. 1 according to an embodiment of the present invention. As shown in FIG. 4, the waveform converting circuit 130 of the present invention comprises a current mode logic (CML) circuit 131 and a frequency divider 132. In structure, the current mode logic circuit 131 is electrically connected to the oscillator controlling circuit 120, and the frequency divider 132 is electrically connected to the current mode logic circuit 131. In practice, the current mode logic circuit 131 may receive the output signal of the oscillator 123 and convert the oscillation waveform into a high frequency oscillation square wave. The high frequency oscillation square wave is a digital format signal. The frequency divider 132 will divide these high frequency oscillation square waves to output a plurality of relative low frequency division square waves. In an embodiment, the waveform converting circuit 130 set up a fixed frequency divider 132 through the types of the expected dielectric material 800 first. In an alternative embodiment, the waveform converting circuit 130 cascades more frequency dividers 132 that divide the input frequency by 2, 4, 8, 16, etc. The waveform converting circuit 130 will decide the amount of the frequency dividers 132 based on the frequency of the oscillation waveform in the oscillator controlling circuit 120 through the internal computing. The frequency of these frequency division square waves is less than but is directly proportional to the frequency of the original oscillation square waves.

The output voltage of the current integrator 144 continues changing due to the reference current source 143 that is controlled by the switching circuit 142 and sets a value of the reference voltage stops the output voltage changing to read the number of the turned-on states. As shown in FIG. 5, the counting readout circuit 140 of the present invention comprises a voltage comparator 145, a pulse generator 146, and a readout circuit 149. In structure, the voltage comparator 145 is electrically connected to the current integrator 144 and the switching counter 141, the pulse generator 146 is electrically connected to the voltage comparator 145 and the current integrator 144, and the readout circuit 149 is electrically connected to the switching counter 141. In practice, the output voltage of the current integrator 144 continues changing due to the reference current source 143 controlled by the switching circuit 142, the voltage comparator 145 is configured to compare the value of the output voltage from the current integrator 144 with the value of the reference voltage. When the value of the output voltage reaches the default value of the reference voltage, which is set in the voltage comparator 145, the switching counter 141 stops counting. To clear the charge in the current integrator 144 is be easy for the next detection when the switching counter 141 stops counting. The pulse generator 146 is configured to generate the pulse voltage to reset the current integrator 144 when the value of the output voltage reaches the default reference voltage. The integrated charging current integrator 144 may clear the initial charge. The readout circuit 149 is configured to read the number of the turned-on states when the value of the output voltage reaches the default value of the reference voltage.

Figure 6:
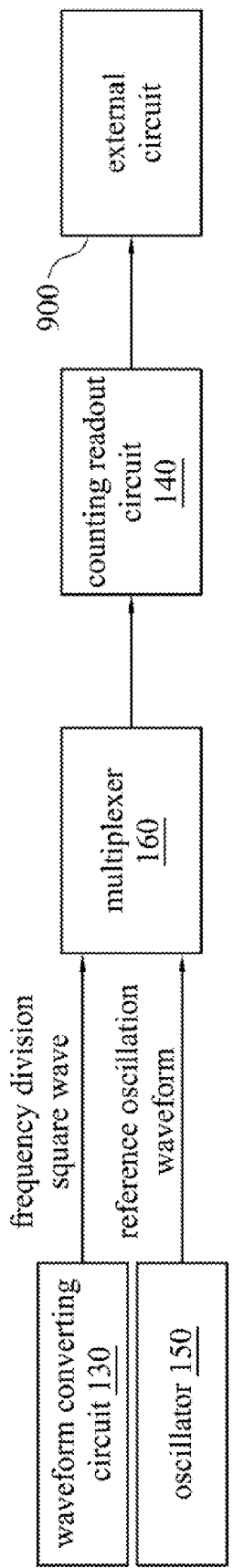
FIG. 6 is a schematic diagram showing a counting readout circuit according to another embodiment of the present invention.

Alternatively, the known frequency standard oscillation waveform is imported to the counting readout circuit 140. The number of the turned-on states of the switching circuit 142 is detected from the switching counter 141, and the number of the turned-on states of the switching circuit 142 is set as the standard number of the turned-on states. The frequency of the frequency division square waves may be calculated based on the standard frequency of the turned-on state of the switching circuit 142, and the oscillation frequency of the oscillation waveform may be calculated based on the frequency of the frequency division square waves. As shown in FIG. 6, in another embodiment, the dielectric constant measurement circuit 100 comprises an accurate frequency oscillator 150 (such as a crystal oscillator) and a multiplexer 160. In structure, the oscillator 150 is electrically connected to the multiplexer 160, and the multiplexer 160 is electrically connected to the waveform converting circuit 130 and the counting readout circuit 140. In practice, the oscillator 150 generates the known frequency standard oscillation waveform. The known frequency standard oscillation waveform is transmitted to the counting readout circuit 140 through the multiplexer 160, and the switching counter 141 reads the standard number of the turned-on states of the switching circuit 142. The frequency division square wave generated from the waveform converting circuit 130 through the multiplexer 160 is transmitted to the counting readout circuit 140 and the switching counter 141 reads the number of the turned-on states of the switching circuit 142. The standard oscillation waveform and the frequency division square waves in sequence are transmitted to the counting readout circuit 140 through the multiplexer 160, the switching counter 141 separately reads the standard number of the turned-on states and the number of the turned-on states of the switching circuit 142 then sends to the external circuit 900 for calculation. In the external circuit 900, the oscillation frequency of the oscillation waveform can be calculated accurately through the standard number of the turned-on states of the switching circuit 142 and the known frequency standard oscillation waveform of the oscillator 150.

When the switching circuit 142 is turned on so that the reference current source 143 can charge the current integrator 144, both the noise power and the signal power within the current integrator 144 may increase. When the charging time is t, the range of the noise frequency increasing within the current integrator 144 is directly proportional to $\sqrt{t}$, and the range of the signal frequency increasing within the current integrator 144 is directly proportional to t. Therefore, in the current integrator 144 the increasing range of the signal-to-noise ratio is directly proportional to $\sqrt{t}$. Accordingly, the signal-to-noise ratio may increase due to the charging time increasing, and the accuracy and the resolution of the number of the turned-on states detected also may increase due to the charging time increasing. In an embodiment, setting an integration counter 147 and a digital comparator 148 in the counting readout circuit 140 to lengthen the integrated charging time of the current integrator 144, and it may improve the resolution of detecting the number of the turned-on states. In the structure, the integration counter 147 is electrically connected to the pulse generator 146, and the digital comparator 148 is electrically connected to the integration counter 147, the switching counter 141, and the readout circuit 149. In practice, the integration counter 147 is configured to accumulate the number of the integration cycles when receiving the pulse voltage. The number of the integration cycles increases by one when the value of the output voltage of the current integrator 144 reaches the value of the reference voltage. The pulse generator 146 generates a pulse voltage to reset the current integrator 144 then makes the value of the output voltage from the current integrator 144 return to the initial value of the output voltage preparing for the next integrated charging cycle. Setting a predetermined number of the cycles that the current integrator 144 is integrated charging in the system beforehand will avoid the current integrator 144 integrated charging endlessly. The digital comparator 148 is configured to compare the number of the integration cycles with the predetermined number of the cycles set in the digital comparator 148. The switching counter 141 continues counting when the number of the integration cycles does not reach to the predetermined number of the cycles. The switching counter 141 stops counting when the number of the integration cycles reaches to the predetermined number of the cycles.

Figure 7:
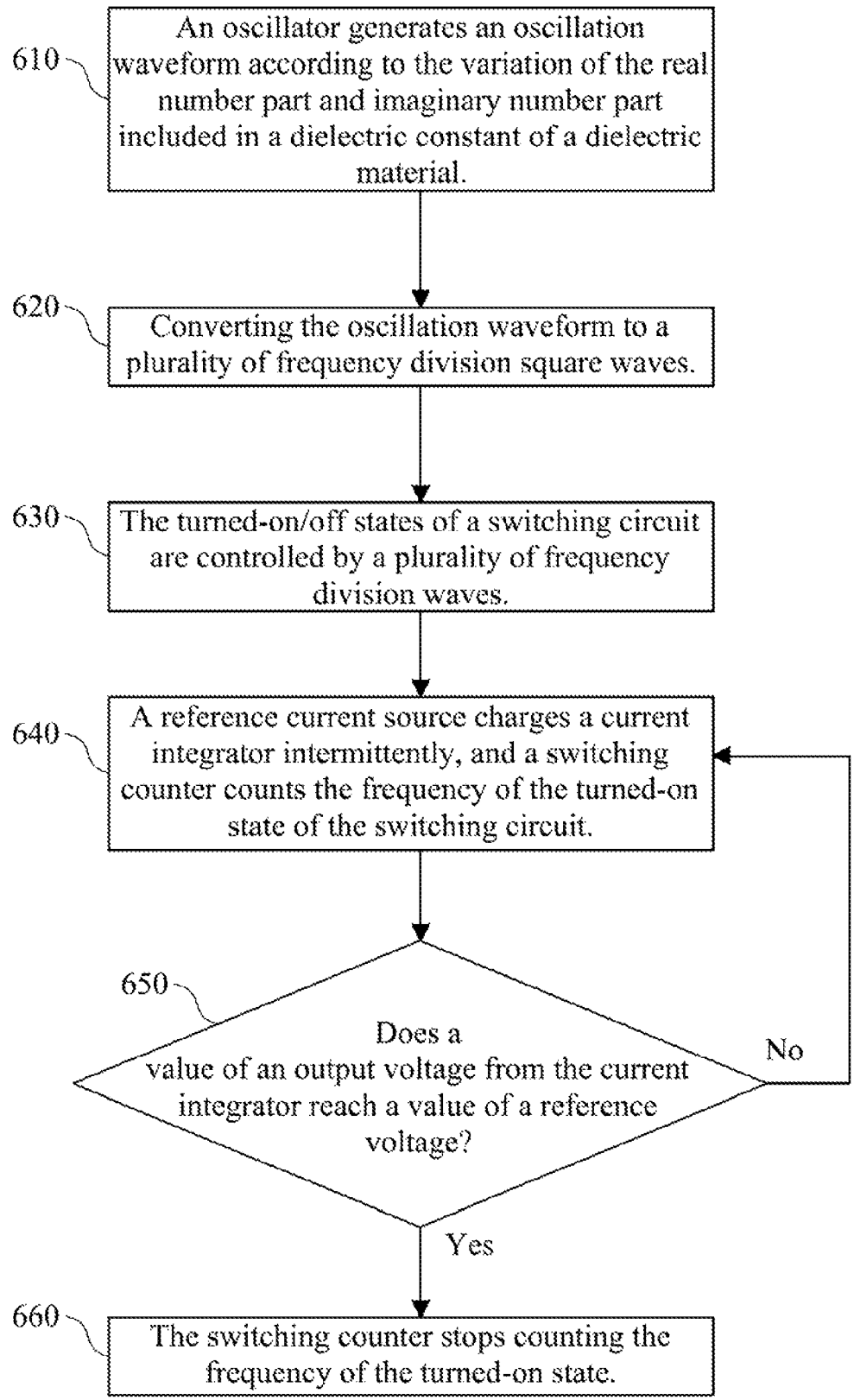
FIG. 7 is a flow chart of a dielectric constant measurement method according to an embodiment of the present invention.

FIG. 7 is a flow chart of a dielectric constant measurement method according to an embodiment of the present invention. As shown in FIG. 7, in step 610, an oscillation waveform is generated according to the response of a dielectric material for a dielectric constant sensor. In step 620, the oscillation waveform is converted into a plurality of frequency division square waves. In step 630, the turned-on/off states of a switching circuit are controlled by a plurality of frequency division waves. In step 640, a reference current source charges a current integrator intermittently through the switching circuit, and a switching counter counts the number of the turned-on states of the switching circuit. In step 650, if a value of an output voltage from the current integrator does not reach a value of a reference voltage, return to step 640, i.e., the reference current source charges the current integrator intermittently through the switching circuit, and the switching counter counts the number of the turned-on states of the switching circuit. But if the value of the output voltage from the current integrator reaches the value of the reference voltage, in step 660, the switching counter stops counting the number of the turned-on states of the switching circuit. The number of the turned-on states of the switching circuit will be read and sent to an external circuit. The external circuit figures out an oscillation frequency of the oscillation waveforms based on the number of the turned-on states, the time from an initial value of the output voltage to the value of the reference voltage for the output voltage of the current integrator, and the other relative adjustable parameters.

The dielectric constant sensor converts the response based on the dielectric material into more parameters that may be processed by the dielectric constant measurement circuit, and then processes and analyze these parameters to achieve the purpose of distinguishing the dielectric material. In an embodiment, the step 610 of the dielectric constant measurement method may be achieved as the following method: generating the oscillation waveform according to the variation of the real number part and the imaginary number part in the dielectric constant of the dielectric material when the dielectric constant sensor senses the dielectric material. In an embodiment, comparing the amplitude value of the oscillation waveform with the reference value, and controlling the amplitude value of the oscillation waveform at the fixed value. The controlling signal of the bias current may be related to the amplitude of the oscillation waveform and calculate the quality factor of the dielectric constant of the dielectric material. Alternatively, in another embodiment, providing the oscillation a fixed bias current and read the amplitude of the oscillation waveform may calculate the quality factor of the dielectric constant of the dielectric material.

In an alternative embodiment, the step 610 of the dielectric constant measurement method as shown in FIG. 7 may be achieved as the following method: a fixed bias current source provides a fixed bias current to the oscillator then reads the amplitude of the oscillation waveform to calculate the quality factor of the dielectric constant of the dielectric material.

In order to control the switching circuit of the counting readout circuit correctly, the oscillation waveform is converted into the oscillation square waves that controls the switching circuit easier, then the oscillation square waves is converted into the frequency division square waves that is able to make the action of the switching circuit correctly. In an embodiment, the step 620 of the dielectric constant measurement method as shown in FIG. 7 may be achieved as the following method: converting the oscillation waveform into a plurality of square waves. These square waves are divided to generate a plurality of frequency division square waves. The frequency of these frequency division square waves is less than the frequency of the original oscillation square waves.

Because the output voltage of the current integrator continues changing due to the reference current source controlled by the switching circuit, a value of the reference voltage is set to stop the output voltage changing to read the number of the turned-on states. In an embodiment, the step 650-step 660 of the dielectric constant measurement method as shown in FIG. 7 may be achieved as the following method: comparing the value of the output voltage from the current integrator with the value of the reference voltage. The current integrator stops counting when the value of the output voltage from the current integrator reaches the default value of the reference voltage. A pulse generator generates a pulse voltage to reset the current integrator when the value of the output voltage from the current integrator reaches the default value of the reference voltage. The current integrator is an integrator. Finally, the number of the turned-on states of the switching circuit counted is read in the switching counter.

Alternatively, in another embodiment, the dielectric constant measurement method uses an accurate frequency oscillator (such as a crystal oscillator) to generate a known frequency standard oscillation waveform, and the standard number of the turned-on states of the switching counter can be read through the dielectric constant measurement method in step 640-660 of the FIG. 7. The number of the turned-on/off states read from the switching counter in step 610-660 of the dielectric constant measurement method is compared with the standard number of the turned-on states, then the oscillation frequency of the oscillation waveform may be calculated to generate based on the response of the dielectric material from the dielectric constant sensor.

In the dielectric constant measurement method, when the switching circuit is turned on to make the reference current source integrated charging to the current integrator, the signal-to-noise ratio may increase due to the charging time increasing, and the accuracy and the resolution of the number of the turned-on states read also may increase due to the charging time increasing. In an embodiment, in order to promote the resolution of the number of the turned-on states read, the number of the integration cycles is accumulated when receiving the pulse voltage. At the time, the pulse voltage may reset the current integrator to make the current integrator returning to go to the next time integrated charging. In order to avoid the current integrator integrated charging endlessly, the default number of the integration cycles is set in the system to stop the integrated charging cycle, and the number of the integration cycles is compared with the predetermined number of the cycles. The switching counter continues counting when the number of the integration cycles does not reach to the predetermined number of the cycles. The switching counter stops counting when the number of the integration cycles reaches to the predetermined number of the cycles.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A dielectric constant measurement circuit, comprising:
   a dielectric constant sensor;
   an oscillator controlling circuit electrically connected to the dielectric constant sensor, and comprising an oscillator configured to generate an oscillation waveform according to a variation of a real number part and an imaginary number part in a dielectric constant of a dielectric material generated by the dielectric constant sensor sensing the dielectric material;
   a waveform converting circuit electrically connected to the oscillator controlling circuit, and configured to convert the oscillation waveform into a plurality of frequency division square waves; and
   a counting readout circuit electrically connected to the waveform converting circuit, and comprising a switching counter, a switching circuit, a reference current source, and a current integrator, wherein the turned-on/off states of the switching circuit are controlled by the frequency division square waves so that the reference current source charges the current integrator intermittently through the switching circuit, the switching counter counts the number of the turned-on states of the switching circuit, and the switching counter stops counting the number of the turned-on states of the switching circuit when an value of an output voltage from the current integrator reaches a value of a reference voltage, and the number of the turned-on states of the switching circuit is related to an oscillation frequency.

2. The dielectric constant measurement circuit of claim 1, the oscillator controlling circuit further comprising:
   an amplitude comparator electrically connected to the oscillator, and configured to compare the amplitude of the oscillation waveform with a reference value to generate a compared result; and
   a current controller electrically connected to the amplitude comparator and the oscillator, and configured to determine a bias current based on the compared result so as to control the amplitude of the oscillation waveform to be maintained at the fixed value.

3. The dielectric constant measurement circuit of claim 1, the oscillator controlling circuit further comprising:
   a fixed bias current source electrically connected to the oscillator and configured to provide a fixed current to the oscillator; and
   an amplitude readout device electrically connected to the oscillator and configured to read the amplitude of the oscillation waveform.

4. The dielectric constant measurement circuit of claim 1, the counting readout circuit further comprising:
   a voltage comparator electrically connected to the current integrator and the switching counter, configured to compare the value of the output voltage with the value of the reference voltage, so that the switching counter stops counting when the value of the output voltage reaches the value of the reference voltage;
   a pulse generator electrically connected to the voltage comparator and the current integrator, and configured to generate a pulse voltage to reset the current integrator when the value of the output voltage reaches the value of the reference voltage; and a readout circuit electrically connected to the switching counter and configured to read the number of the turned-on states of the switching circuit.

5. The dielectric constant measurement circuit of claim 1, the counting readout circuit further comprising:

an integrated counter electrically connected to the pulse generator and configured to accumulate the number of integration cycles whenever receiving the pulse voltage; and a digital comparator electrically connected to the integrated counter, the switching counter, and the readout circuit, being configured to compare the number of integration cycles with a predetermined number of the cycles, the switching counter continuing counting when the number of integration cycles is less than the predetermined number of the cycles, and the switching counter stopping counting when the number of integration cycles is less than the predetermined number of the cycles.

6. A dielectric constant measurement method, comprising:

generating an oscillation waveform according to a variation of a real number part and an imaginary number part in a dielectric constant when a dielectric constant sensor senses a dielectric material;

converting the oscillation waveform into a plurality of frequency division square waves; and controlling the turn-on/off states of a switching circuit based on the frequency division square waves so that the reference current source charges the current integrator intermittently through the switching circuit, counting the number of the turned-on states of the switching circuit, stopping counting the number of the turned-on states of the switching circuit when a value of an output voltage from the current integrator reaches a value of a reference voltage, wherein the number of the turned-on states of the switching circuit is related to an oscillation frequency.

7. The dielectric constant measurement method of claim 6, further comprising:

comparing the amplitude of the oscillation waveform with a reference value to generate a compared result; and determining a bias current based on the compared result so as to control the amplitude of the oscillation waveform to be maintained at the fixed value.

8. The dielectric constant measurement method of claim 6, further comprising:

providing a fixed current to the oscillator; and reading the amplitude of the oscillation waveform.

9. The dielectric constant measurement method of claim 6, further comprising:

comparing the value of the output voltage with the value of the reference voltage so that the switching counter stops counting when the value of the output voltage reaches to the reference voltage;

generating a pulse voltage to reset the current integrator when the value of the output voltage reaches to the value of the reference voltage; and reading the number of the turned-on states of the switching circuit.

10. The dielectric constant measurement method of claim 6, further comprising:

accumulating the number of integration cycles whenever receiving the pulse voltage; and comparing the number of integration cycles with a predetermined number of the cycles, the switching counter continuing counting when the number of integration cycles is less than the predetermined number of the cycles, and the switching counter stopping counting when the number of integration cycles is less than the predetermined number of the cycles.

* * * * *